United States Patent [19] [11] 4,256,833
Ali et al. [45] Mar. 17, 1981

[54] ENZYME IMMUNOASSAY FOR ALLERGIC DISORDERS

[76] Inventors: Majid Ali, 19 Edgemont Pl., Teaneck, N.J. 07666; Donald Nalebuft, 89 Lake Shore Dr., Oakland, N.J. 07436; Alfred Fayemi, 15 Francine Ct., White Plains, N.Y. 10607; Madhava P. Ramanarayanan, 100 Haven Ave., New York, N.Y. 10032; Ricardo Mesa-Tejada, 42 Juniper Pl., Briarcliff Manor, N.Y. 10510

[21] Appl. No.: 1,874

[22] Filed: Jan. 8, 1979

[51] Int. Cl.³ .................. C12Q 1/66; C12N 11/02; C12N 9/96
[52] U.S. Cl. .................................. 435/7; 435/177; 435/188; 435/192; 23/230 B; 424/12
[58] Field of Search .................. 435/7, 174, 188, 177, 435/192; 23/230 B; 424/8, 12

[56] References Cited

U.S. PATENT DOCUMENTS

| 3,905,871 | 9/1979 | Rubenstein et al. | 435/7 |
| 4,031,197 | 6/1977 | Marinkovich | 424/12 |
| 4,069,105 | 1/1978 | Singh | 435/188 |
| 4,115,539 | 9/1978 | Eisenhardt et al. | 424/12 |

OTHER PUBLICATIONS

Berezin et al., "Catalytic Properties and Thermostability of Horseradish Peroxidase Covalently Bound to Sepharose Through Carbohydrate Residues of the Enzyme", *Chem. Abstracts*, vol. 87, No. 23, p. 165 (1977) abs. #35084d.

Mukajima, et al., "Enzyme Immunoassay Using Multiple Antigen Enzyme Complex", *Chem. Abstracts*, vol. 87, No. 23, p. 269 (1977) abs. #180244K.

March, *Advanced Organic Chemistry: Reactions, Mechanisms, and Structures*, McGraw-Hill Book Co., New York (1968) pp. 890, 891.

*Primary Examiner*—Thomas G. Wiseman
*Attorney, Agent, or Firm*—Ostrolenk, Faber, Gerb & Soffen

[57] ABSTRACT

Horse radish peroxidase (HRP) is treated with phenyl isothiocyanate (PITC) to block the free amino groups on the enzyme. The PITC derivative of HRP is treated with periodate to oxidize the carbohydrate moiety on the enzyme, thus generating aldehyde groups. Gamma G globulin fraction (IgG) purified from an anti-human IgE serum is conjugated to the peroxidase-aldehyde by formation of a Schiff's base between the aldehyde group on the enzyme and the amino groups on the IgG. The Schiff's base is stabilized by reduction using the optimal amounts of sodium borohydride determined by tiration. A stable HRP-anti IgE IgG conjugate prepared thus is employed in a solid phase enzyme immunoassay for the detection of allergen specific IgE. The results of this assay can be used to determine a safe initial hypersensitization dosage level.

8 Claims, 1 Drawing Figure

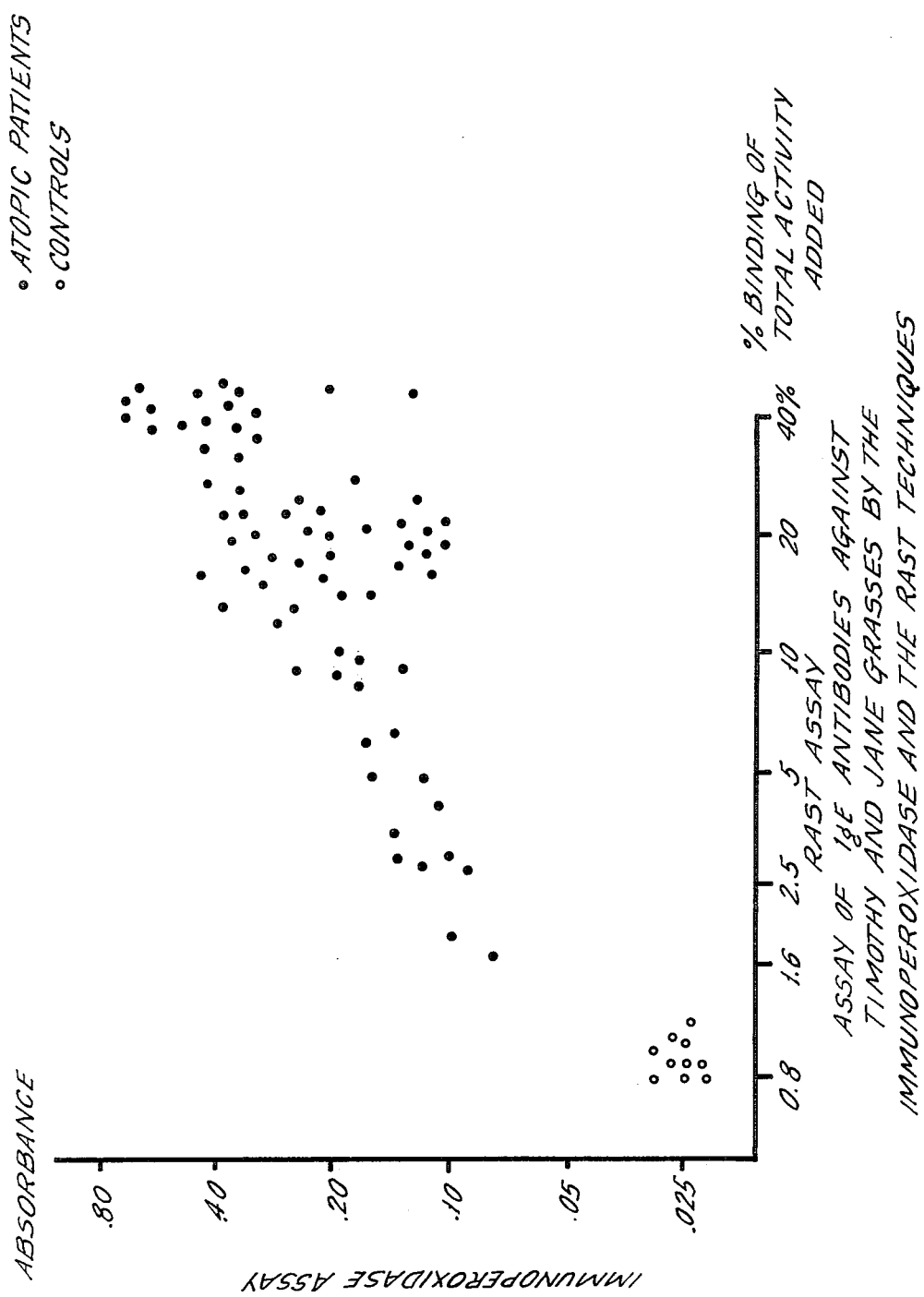

ENZYME IMMUNOASSAY FOR ALLERGIC DISORDERS

BACKGROUND OF THE INVENTION

In 1966, Ishizaka established that the human allergen reaginic antibodies belong to a distinct class of immunoglobulins, IgE. There followed a decade of remarkable sequence of events. Sensitization of the human and monkey skin to Prausnitz-Kunster reaction by IgE antibodies was demonstrated. It was recognized that the role of IgE is central to the release mechanisms of chemical mediators of anaphylaxis; it mediates immunologic release of histamine from human leucocytes and mast cells; it primes the human lung tissue for antigen-induced release of histamine and Slow Reacting Substance of Anaphylaxis; it triggers the release of eosinophil chemotactic factor from human lung; and its avidity for attachment, through its Fc portion, to the receptors on the surface of mast cells and basophil granules was shown. It has been inferred that the number and the affinity of IgE antibodies bound to the basophil granulocytes determines the sensitivity of this cell to the allergen, while the histamine release induced by the antigen-antibody reaction on the cell surface is the function of the intracellular enzyme system and cyclic AMP level.

Dating back to the early part of the 20th century, patients with hay fever were treated with injections of incriminated allergens, albeit without understanding the pathologic bases of the disease or the pharmacologic bases for the efficacy of the therapy. Johansson's observation, in 1967, of augmented levels of serum IgE in atopic patients sparked intense interest in this relationship; individuals with inhalant allergies were found to display seasonal peaks in their serum IgE levels; abatement of allergic symptomatology with immunotherapy was documented. Partial suppression of seasonal peaks following specific immunotherapy was demonstrated and the inter-relationship of levels of IgE and IgG in atopic subjects, and the changes induced by specific immunotherapy have been illuminated.

The major in vitro test used to determine IgE today is a radioimmunoassay technique known as the Radio Allergo Sorbant Test or RAST.

The advent of enzyme-labelled antibodies has been a major event in the progress of immunoassays. The use of such enzyme labels, for this purpose introduced in 1971, offers several advantages over radioimmunoassay techniques including the freedom from hazards of radioactive material, the stability of a label for months and possibly longer, the use of photometric rather than radiometric equipment, and at times, elimination of separation procedures. For these reasons, enzyme immunoassays have found wide-spread and diversified application both in reasearch and in clinical practice.

In 1966, Nakane & Pierce published a report demonstrating that peroxidase could be coupled to an antibody by a simple procedure to produce a stable conjugate. The intact immunological reactivity of such a conjugate was shown to render it eminently suitable for use in immunotracing methods, in a fashion similar to that of fluorescein-labelled antibody. Since that time a number of conjugates have been developed and used for enzymatic immunological tests. See, e.g., U.S. Pat. Nos. 4,016,043 and 3,645,852.

For the assay of total IgE in serum, alkaline phosphatase has been employed as the enzyme marker in an application of the enzyme linked immunosorbant assay and in a magnetic enzyme imminoassay. The use of both alkaline phosphatase and galactosidase has been described for the assay of allergen-specific IgE antibodies.

The success in terms of quantitation, sensitivity and absence of non-specific reaction in any solid phase immunoenzymatic technique depends, to a great extent, on the quality of the enzyme-antibody conjugate. The immunoenzymatic techniques described in the literature for use with IgE have been performed using conjugates prepared by means of bifunctional reagents. Thus, the use of alkaline phosphatase (Mol. Wt. 60,000) or galactosidase (molecular weight 580,000) as enzyme markers has required the use of glutaraldyhde for conjugation of the enzyme to the antibody. The negative controls of such procedures exhibit a high degree of background activity or interference which interferes with the readability, i.e., interpretation, of the test results. While no precise quantitation has been reported, we have found that the use of alkaline phosphate and galactosidase as enzyme markers has resulted in the final yield of a very small amount of functionally usable conjugates, usually 30% or less, and unacceptable contamination with large amounts of side reaction products. Such byproducts include enzyme-enzyme conjugates, IgG-IgG conjugates and large aggregates. The separation of the usable conjugate from the undesirable side reaction products has been tedious and time consuming and, in addition, the stability of the purified fraction has not been satisfactory.

It has now been determined that an in vitro solid phase immunoenzymatic allergy test for the presence of IgE which is very successful in terms of quantification, sensitivity and absence of non-specific reaction can be realized if the enzyme employed is Horse radish peroxidase (HRPO, molecular weight 40,000) and if the conjugate is prepared using enzyme with its free amino groups blocked with phenylisothiocyanate as the first step, and if the reduction of the conjugate is carried out by titration. When the test is carried out according to the method of the present invention, the results are such that a safe initial hypersensitization dose can be determined from the results.

Accordingly, it is the object of this invention to provide a new and improved method and reagents for carrying out an immunoenzymatic test for the presence of allergen specific IgE and for the use of the test results in hypersensitization therapy. This and other objects of the invention will become apparent to those skilled in this art from the following detailed description.

SUMMARY OF THE INVENTION

This invention relates to an improved allergy test, a reagent therefor, and the correspondence of such tests with hypersensitization therapy. More particularly, the improved test uses a horse radish peroxidase marked antibody which has been prepared using phenylicothiocyanate as a blocking agent and reduced by titration and with which the enzymatic activity, after the test procedure (immunoenzymatic assay) has been completed, can be used to determine a safe initial hypersensitization dosage level.

DESCRIPTION OF THE INVENTION

The method of the present invention can be performed with any biologic fluid of the patient to be tested. Thus, blood and suitable fluids include nasal, bronchial, middle ear, gastric, and lacrimal secretions. In the first step of the process, the biologic fluid is contacted with anti-IgE or allergen which is preferably bound to a substrate. Any suitable substrate can be used such as cellulose or any other cellulosic material such as paper or synthetic supports in the form of tubes, microtitre plates or any other physical form of the material such as nylon, polystyrene, polypropylene or polycarbonate, and biological material such as red blood cells. Some of the solid phase media with anti-IgE or allergen fixed thereon are available in commerce. The length of contact should be sufficient to permit the reaction between IgE in the biologic fluid and the bound anti-IgE or the allergen and is generally about 0.1-10 hours or more.

After the contacting, the substrate is preferably although not necessarily washed to remove unbound material with any suitable inert liquid, such as a phosphate buffered saline having a pH of about 7.4.

In the next step of the process, the substrate is contacted with peroxidase conjugated anti-human IgE for a time sufficient to permit the reaction between the enzyme marked antibody and the IgE bound to the substrate. Generally, incubation is permitted to proceed for about 1-4 hours, preferably about 2 hours, at room temperature (temperature range 20° to 25° C.) and in the presence of an optional incubation buffer such as the aforementioned phosphate buffered saline with or without additives. It will be recognized that variation in the incubation time and conditions is possible and the same is well within the skill of those in this art. Following the incubation, the substrate is again preferably although not necessarily washed with a suitable inert liquid such as the buffer heretofore mentioned.

The enzymatic activity of the solid phase substrate can now be determined by a variety of procedures known in the art. One procedure which is presently preferred involves the contacting of the substrate with a chromogenic system which will react with the conjugated enzyme to develop color. Any chromogenic reagent which reacts with the conjugate to develop color can be employed in this step. The reagent presently preferred contains hydrogen peroxide and o-phenylene diamine. Other chromogenic systems containing p-phenylene diamine, 5 aminosalicylic acid, o-dianisidine, pyrogallol and the like can also be used. The reagent is conveniently employed in the form of a solution in an inert carrier such as phosphate buffered saline or any other suitable buffer. The substrate is contacted with the chromogenic reagent for a time sufficient to allow color to develop which is usually about 0.1-3 hours and preferably about 0.75-1.25 hours. The contacting temperature is preferably ambient. Results can be noted by simple observation or by the use of automatic equipment which measure absorbance at the absorption maximum of the reaction product (e.g. 492 nm for o-phenylene diamine) against a blank reagent and provide a net value.

In order to obtain a high degree of quantification, sensitivity and absence of non-specific reaction in the solid phase immunoenzymatic determination of IgE, it is necessary that the enzyme be HRPO. The peroxidase is conjugated to IgG by first blocking the free amino groups on the peroxidase molecule with a blocking agent, then oxidizing its carbohydrate moiety with periodate to yield the peroxidase aldehyde, and after dialysis, the peroxidase aldehyde is linked to the amino group of the IgG molecule by formation of a Schiff's base which is thereafter stabilized by reduction with a suitable reagent such as sodium borohydride or sodium cyanoborohydride. The sequence of reactions just described is known. In the present invention, it was necessary to modify the sequence in two respects. First, the blocking reagent must be phenylisothiocyanate. The use of conventional blocking reagents such as fluorodinitrobenzene results in non-specific reaction, presumably because of the increased negative charge on the enzyme molecule, when the immunoenzymatic test is carried out. The blocking agent is prepared as a solution in absolute ethanol, since it is easily soluble in this organic solvent; and when added as an ethanolic solution to the peroxidase solution the low concentration of ethanol introduced would not be harmful to the enzyme. In order to minimize the removal of excess blocking agent, the agent is added drop by drop while stirring the receiving enzyme solution until a slight cloudiness is observed in the reaction mixture, indicating a slight excess of the reagent.

A second important aspect of the preparation of the conjugate regards the borohydride reduction. It is known that samples of sodium borohydride are somewhat unstable being particularly sensitive to exposure to moisture. As a result, a sample of sodium borohydride gradually deteriorates in its reducing power depending on conditions of storage and depending on how many times the bottle has been opened and closed between uses. For the reduction of the Schiff's base formed between IgG fraction of anti-human IgE and the peroxidase aldehyde, it is necessary that the optimal amount of reducing power derived from the borohydride be used, since a lower amount reduces the efficiency of conjugation, and an excess leads to the formation of insoluble aggregates, and thus decreases the final yield of the useful conjugate. We have found that adding a predetermined amount of sodium borohydride to the peroxidase aldehyde-IgG has resulted in conjugates in differing yields from time to time. Therefore we have worked out a titration procedure which assumes reasonably reproducible amounts of the conjugate. In this procedure a given concentration of sodium borohydride is freshly prepared minutes before use. To the peroxidase aldehyde solution, to which has been added the appropriate amount of IgG fraction of antihuman IgE, is now added small quantities of the borohydride solution step by step till the color of the mixture develops a slight reddish tinge.

Because of the high degree of quantification, sensitivity and the absence of non-specific reaction, it is possible to identify a safe initial hypersensitization dosage amount from the results of the above described test. Heretofore such therapy has been carried out starting with extremely dilute dosage which was increased with the passage of time. As is apparent, relatively weak atopic patients can tolerate a higher dosage and in fact, the higher dosage is necessary in order to realize the desired hypersensitization results. However, since there was no way to determine whether a greater dosage level would be safe for the patient, it was necessary to begin therapy with an extremely dilute amount.

It has been found that serum samples tested by the above described method can be divided into five distinct groups. Those serums whose net absorbance (sample minus control) fall within the range of 0.1-0.5 are considered negative results. For a net absorbance of 0.5-0.75, the results are very weakly positive. An absorbance of 0.75-1.2 is considered weakly positive, from 1.2–2 positive and greater than 2 strongly positive. Individuals whose sera test in the negative group usually do not require hypersentization treatment. Those in the very weakly positive group are usually provided with treatment only if their history so indicates and in that case, the initial dosage is the same as that for the weakly positive group. Atopic individuals whose sera test in the weakly positive group can receive hypersensitive treatment at 1:500 w/v safely, those in the positive group can receive 1/5000 w/v safely and those in the strongly positive group can usually receive 1/50,000 w/v safely.

In our work, we have preferred to use rabbit antihuman IgE because it has been found that a significant loss of the test specificity may result from the presence of heterophile antibodies in the test serum which may non-specifically bind the goat or sheep immunoglobulins to the allergen. The use of chick serum has been found quite suitable for the dual purpose of maintaining the optimum protein concentration as the sample is diluted with the incubation buffer and for reducing the non-specific cross-reactivity between the various proteins and the sample and the antiserum. Aprotinin (Trasylol) is preferably added to the incubation buffer to inhibit any protease activity that may exist in the system.

Horse radish peroxidase (crystalline enzyme, Sigma Type VI,R23.0 or higher; used in our work samples c R2 of 3.47) dissolved in 01 M sodium carbonate-bicarbonate buffer, pH 8.5 to a final concn. of 5 mg enzyme per ml. To this was added a freshly made solution of phenylisothiocyanate 1% v/v in absolute ethanol, drop by drop (while constantly stirring the enzyme solution gently at room temperature) until a slight cloudiness developed. Usually 0.03 to 0.04 ml of a 1% solution of PITC is needed to achieve this cloudiness per ml of HRP solution 5 mg/ml. It is left standing at room temperature while gently stirring for 2 hrs. If a precipitate, due to an excess of the blocking reagent, appears at this stage, it can be safely removed by centrifugation, and the clear supernatant used for further processing without any significant loss of efficacy of the enzyme. To the enzyme with its free amino groups blocked as mentioned above, was added a 0.06 M sodium periodate solution drop by drop to a final concentration of about 0.03 M thus oxidizing the vicinal dihydroxy groups on the carbohydrate moiety of the enzyme to generate free aldehyde groups. The periodate oxidation, which is time and concentration dependent, is terminated at the end of 20' by the addition of an excess of ethylene glycol which serves to exhaust the unused periodate. This mixture is then dialysed against 1 mM NaOAC-HOAC buffer to remove all the micromolecular products of the reaction (molecules smaller than 12,000 daltons).

The dialysed PITC derivative of HRP in its aldehyde form is now reacted with the IgG fraction at pH 9.5 of antihuman IgE to form a Schiff's base, which is then stabilized by reduction with sodium borohydride under optimal conditions. (Typically in a sample starting with 5 mg HRP and 7.5 mg IgG, one needs about 0.5–0.8 mg NaBH$_4$.) To such a reaction mixture is added an equal volume of neutral saturated amm. sulfate thus precipitating the conjugate, and the precipitated conjugate is separated from unreacted enzyme by centrifugations; the pelleted antibody enzyme conjugate is dissolved in PBS and dialysed against PBS to remove excess salt from the precipitated material. Conjugates prepared by this procedure were found to have an RZ of 0.5–0.6 and were found to contain 2–3 molecules of HRP/IgG assessed by sedimentation techniques. The conjugates maintain their immunologic reactivity and enzyme activity for several months when stored at or below minus 20° C.

Allergen extracts and RAST reference sera A,B,C and D (containing antibirch IgE antibodies in concentrations of 17.5, 3.5, 0.7, and 0.35 Phadebas RAST units (PRU) respectively, were obtained from a commercial source. The allergen extracts were timothy grass, 79,000 PNU/ml and white birch tree, 80,000 PNU/ml. Commercially available polystyrene tubes 12 mm×75 mm were coated by incubating them 1 to 10 uL of antigen extract and 200 uL of coating buffer overnight at 4° C. The coated buffer contained 3.18 grams of sodium carbonate, and 5.86 grams of sodium bicarbonate dissolved in water to 100 ml and diluted 1:20 with distilled water immediately before use, pH 9.6. The tubes were washed with a phosphate buffered saline and stored at −20° C.

The sera for assay of IgE antibodies against timothy grass was obtained from patients with a history of severe allergic systems and RAST scores of Class 1 to 4 for such antibodies. The sera for the control of method specificity was obtained from five individuals without any history of allergic symptoms and with a negative RAST score. The serum of the timothy grass sensitive patient with raised level of serum total IgE was reacted with an inappropriate antigen (birch tree) to demonstrate the independence of this assay from serum total IgE.

The procedural steps for immunoperoxidase assay were carried out as follows. First, an incubation of the test serum (100, 50, 25 and 12.5 uL diluted in incubation buffer to a final volume of 200 uL) overnight at 4° C. in the polystyrene tubes with previously absorbed antigens was effected. The incubation buffer was phosphate buffered saline, pH 7.4, containing 5% chicken serum, 5% trasylol (TM BAYER), 0.1% Tween 20 and 0.1 mM merthsiolate. The tubes were then washed four times with phosphate buffered saline containing 0.1% Tween 20, a vortex between the washes. The above described peroxidase conjugated rabbit antihuman IgE was added to the polystyrene tube (10 ug/ml) and allowed to stand for 2 hours at room temperature in the incubation buffer. The tubes were then washed four times with phosphate buffered saline containing 0.1% Tween 20, vortex between the washes, followed by the addition of 250 uL of a chromogenic reagent of 0.5 mg/ml o-phenylenediamine in an enzyme buffer containing 0.006% of hydrogen peroxide. The enzyme buffer was a freshly prepared McIllvain buffer (36.85 ml 0.1 m citric acid and 63.15 ml 0.2 m Na$_2$HBO$_4$) of pH 6.0. After 1 hour at room temperature, the color reaction was arrested by the addition of five normal sulphuric acid, the color product diluted with 0.5 N H$_2$SO$_4$ and the absorbance at 492 mm was measured against a blank reagent.

Standard curves were constructed for the immunoperoxidase assay of birch tree antigen and compared with that prepared by the radioimmunoassay technique of the RAST test with the same batch of reference sera used for the two procedures. On a log/log scale, the change in absorbance with the immunoperoxidase assay was linear. The standard curves obtained with 12.5, 25 and 50 uL of the test sample were found to be significantly less linear in the lower range (reference sera C and D) than those with 100 uL. The absorbance of the negative control sera for the birch tree antigen was lower than that of the RAST reference serum D.

Data for anti-timothy grass and anti-june grass IgE antibodies for 73 atopic patients with positive history and a positive RAST test result and four clinically non-atopic individuals with a negative RAST test and 6 cord sera is set forth in the FIGURE. The quality control data for the IgE antibodies against timothy and june grass, and short ragweed is given in Tables 1, 2 and 3 below. The difference between the values for the absorbance of the atopic and non-atopic sera is significantly significant.

TABLE 1

Within-batch reproducibility of the immunoperoxidase Assay for IgE antibodies against June and Timothy grasses.

| Allergen | Serum No. | Absorbance Mean* | Range | Coefficient of Variation (%) |
|---|---|---|---|---|
| June grass | 1 | .153 | .150–.160 | 4.57 |
|  | 2 | .123 | .118–.130 | 6.42 |
| Timothy grass | 1 | .096 | .090–.107 | 11.97 |
|  | 2 | .089 | .084–.091 | 11.68 |

*Mean for 6 determinations

TABLE 2

Between-batch variability of the Immunoperoxidase Assay for IgE antibodies against June and Timothy grasses.

| Allergen | Absorbance Mean* | Range | Coefficient of Variation (%) |
|---|---|---|---|
| June grass | .218 | .208–.226 | 8.5 |
| Timothy grass | .070 | .061–.074 | 13.71 |

TABLE 3

The Quality Control data for the Immunoperoxidase Assay for IgE antibodies against short ragweed antigens.

| SERUM | Absorbance Mean | Range | ± 2 SD | Coefficient of Variation (%) |
|---|---|---|---|---|
| Cord serum | .050* | .045–.057 | .008 | 14 |
| Serum #1 | .082** | .073–.090 | .0108 | 13.1 |
| Serum #2 | .223** | .213–.226 | .010 | 4.4 |

*Mean for 10 determinations
**Mean for 6 determinations

The atopic patients can be categorized as weakly (0.075–0.15), moderately (0.15–0.3) or strongly (0.3 and above) positive on the basis of the absorbance test results. The safe hypersensitization dosage can be selected in the light of the above results, e.g., 1/500 w/v for patients in the weakly positive category.

Various changes and modifications can be made in the process and products of this invention without departing from the spirit and scope thereof. The various embodiments disclosed herein were for the purpose of further illustrating the invention but were not intended to limit it.

What is claimed is:

1. A stable peroxidase immunoglobulin conjugate having an average of 2–3 molecules of peroxidase per molecule of immunoglobulin and an RZ value of 0.5–0.6 by reacting a peroxidase which has been previously treated with phenyl isothiobyanate to block its free amino groups and oxidized to form aldehyde groups from its carbohydrate moiety with an immunoglobulin to form a Shiff's base which is titrated with a reducing agent to form the stable conjugate.

2. The conjugate of claim 1 wherein said immunoglobulin is IgG.

3. In an enzyme immunoassay for detecting IgE antibody specific for allergen, in which a test serum is brought into contact with allergens immobilized on a solid phase under binding conditions and then are enzyme-labelled immunoglobulin is contacted with the specific IgE antibodies bound to the solid phase and thereafter the enzyme activity of the solid phase is determined, the improvement which comprises employing the peroxidase labelled immunoglobulin conjugate of claim 1 as said enzyme labelled immunoglobulin.

4. The method of claim 3 wherein the presence of the enzyme is determined by measuring absorbance at 492 nm.

5. The method of claim 4 wherein the net increase of absorbance compared to a control is used to establish an initial hypersensitization therapy dosage level.

6. The method of claim 3 wherein said immunoglobulin is IgG.

7. In a method of preparing an enzyme labelled immunoglobulin Schiff's base by blocking the free amino groups on the enzyme with a blocking agent, oxidizing the carbohydrate moiety of the enzyme to yield the corresponding aldehyde, dialysing the aldehyde and thereafter linking the aldehyde to the amino group of the immunoglobulin by formation of a Schiff's base and stabilizing the Schiff's base by reduction, the improvement which comprises employing peroxidase as the enzyme, employing phenylisothiocyanate as the blocking agent, and controlling the stabilizing reduction by titration.

8. The method of claim 7 wherein said immunoglobulin is IgG.

* * * * *

UNITED STATES PATENT AND TRADEMARK OFFICE
CERTIFICATE OF CORRECTION

PATENT NO. : 4,256,833

DATED : March 17, 1981

INVENTOR(S) : Majid Ali, et al

It is certified that error appears in the above-identified patent and that said Letters Patent are hereby corrected as shown below:

Under the headings for the Inventors, for "Nalebuft" read -- Nalebuff --.

In the Abstract, third word from the end, for "hypersensitization" read -- hyposensitization --.

Column 2, lines 43, 49, 56 and 62-63, for "hypersensitization" read -- hyposensitization --; and line 58 for "phenylicothi" read -- phenylisothi --.

Column 4, lines 51 and 58, for "hypersensitization" read -- hyposensitization --.

Column 5, lines 3 and 8, for "hypersensitization" read -- hyposensitization --.

Column 7, line 53 for "hypersensitization" read -- hyposensitization --.

UNITED STATES PATENT AND TRADEMARK OFFICE
CERTIFICATE OF CORRECTION

PATENT NO. : 4,256,833
DATED : March 17, 1981
INVENTOR(S) : Majid Ali, et al

It is certified that error appears in the above-identified patent and that said Letters Patent are hereby corrected as shown below:

Column 8, line 12, after "RZ" read -- (Reinheit Zahl) --; line 13, before "by" read -- prepared --; line 14 for "isothiobyanate" read -- isothiocyanate --; line 24, delete "are"; and line 36, for "hypersensitization" read -- hyposensitization --.

Signed and Sealed this

Twenty-second Day of September 1981

[SEAL]

Attest:

GERALD J. MOSSINGHOFF

Attesting Officer

Commissioner of Patents and Trademarks